United States Patent [19]

Bain et al.

[11] Patent Number: 4,652,532

[45] Date of Patent: Mar. 24, 1987

[54] FREE RADICAL BASED BIOCHEMICAL METHOD FOR DETECTING SUBSTANCES IN FLUIDS

[76] Inventors: James D. Bain, 5661 Dorothy Way, San Diego, Calif. 92115; Billy L. Lasley, 3152 Grenada Ave., San Diego, Calif. 92104

[21] Appl. No.: 686,073

[22] Filed: Dec. 24, 1984

[51] Int. Cl.$^4$ .................. G01N 33/53; G01N 33/532; G01N 33/537

[52] U.S. Cl. .................................. 436/501; 436/536; 436/538; 436/803; 436/817

[58] Field of Search ............... 436/803, 501, 536, 538, 436/817

[56] References Cited

U.S. PATENT DOCUMENTS

| | | | |
|---|---|---|---|
| 3,690,834 | 9/1972 | Goldstein | 436/803 X |
| 3,888,866 | 6/1975 | Leute | 436/803 X |
| 3,959,287 | 5/1976 | Goldstein | 436/803 X |
| 4,045,420 | 8/1977 | Soffer | 436/803 X |
| 4,123,431 | 10/1978 | Soffer | 436/803 X |
| 4,160,645 | 7/1979 | Ullman | 436/803 X |

OTHER PUBLICATIONS

Tan, C. et al., "Membrane Immunoassay: A Spin Membrane Immunoassay for Thyroxine," *Methods in Enzymology*, Eds. J. Langone and H. Vinakis, Academic Press, New York, 1981, 74:151–161.

Yang, G., and E. Copeland, "Spin Immunoassay," *Methods in Enzymology*, Eds. J. Langone and H. Vinakis, Academic Press, New York, 1981, 74:140–151.

*Primary Examiner*—Sidney Marantz
*Attorney, Agent, or Firm*—Brown, Martin, Haller & Meador

[57] ABSTRACT

A biochemical method of assaying for ligand molecules in fluids based on the specific interaction of a ligand and a ligand-recognition molecule that binds the ligand wherein a free radical forming group is covalently coupled to label either a ligand sought to be assayed or the ligand recognition molecule or is internally generated from the ligand or ligand recognition molecule, and directly or indirectly assaying for the ligand.

14 Claims, No Drawings

FREE RADICAL BASED BIOCHEMICAL METHOD FOR DETECTING SUBSTANCES IN FLUIDS

BACKGROUND OF THE INVENTION

A variety of techniques as described in the *Methods of Enzymology*, Vols. 70–73, Ed. J. J. Langone and H. U. Unhais, Academic Press, 1981, are routinely used to assay fluids for molecules present in micromolar amounts or less, that are indicative of disease, or alterations in the normal physiology of a living system. Nearly all of these techniques are premised on the use of molecules that specifically recognize the molecule sought to be assayed, the former being termed a ligand-recognition molecule, and the latter a ligand. Perhaps the best example is the detection of antigen with antibody, although, as described by Erb, L. et al in *Steroids* Vol. 39, p. 33 (1981) other nonimmune related specific binding receptors have been used. Generally such assays involve the formation of a complex, either in solution, or on a solid surface, of a labelled ligand bound to a ligand-recognition molecule. The amount of ligand in the fluid sought to be assayed is determined by its ability to either compete off ligand from the ligand-recognition molecule subsequent to complex formation, or to compete with ligand for binding to the ligand-recognition molecule simultaneous to complex formation. Since the resulting amount of labelled ligand bound to the ligand-recognition molecule is inversely related to the amount of ligand present in the fluid, the presence of the latter can be ascertained and/or quantitated. A second method of detecting ligands is to label the ligand-recognition molecule such that the amount of ligand-recognition molecule detected reflects the amount of complex formed which is in turn a function of ligand concentration present in the fluid being assayed.

Both ligands or ligand-recognition molecules are commonly labelled either by direct covalent attachment of radioactive atoms, such as $125_I$, to the molecule, or by synthesis of the ligand or ligand-recognition molecule using radioactive starting materials so as to incorporate radioactive atoms into their structure. In lieu of using radio labels, ligands or ligand-recognition molecules can be labelled by covalent attachment of either fluorescent or enzymatic molecules. The latter, when incubated with the appropriate substrate give readily detectable color reactions, and is termed ELISA (Enzyme Linked Immunosorbant Assay).

The presently used immunoassays are sensitive and versatile enough to detect most ligands. Nonetheless, these assays have some undesirable features. Notably they rely on the use and detection of radioactive substances which necessarily require expensive instrumentation, generally scintillation or gamma counters, in either a medical or research setting. Also, because of the heightened awareness of the dangers associated with radiation, it is becoming increasingly difficult, partly due to newly implemented state regulations, to dispose of such substances after they have been used. Thus, other less expensive methods of performing immunochemical assays that do not use radioactive labels are desirable. To some extent the detection of ligands or ligand-recognition molecules based on enzyme labels have circumvented the problems associated with the use of radioactive tracers. Nevertheless, these assays have certain limitations, the major one being the large size of the enzymes used which, when bound to the ligand or ligand-recognition molecule, have the potential to alter their normal structure and hence mask their recognition sites.

SUMMARY OF THE INVENTION

According to the present invention, a liquid or solid phase free radical based chemical method for detecting ligand molecules is described that relies on the formation of a ligand/ligand-recognition molecule complex wherein either part of the complex carries a free radical forming molecule suitable for detection. To detect the concentration of ligand in fluids the latter is mixed either simultaneously with labelled ligand to the ligand-recognition molecule, or added subsequent to complex formation, and ligand present in the fluid allowed to compete for binding to the ligand-recognition molecule. Alternatively, the ligand-recognition molecule may carry the label and be added to the fluid to be assayed. The amount of labelled ligand bound to the ligand-recognition molecule or alternatively the amount of labelled ligand-recognition molecule present in the complex is determined by separating the bound from unbound reactants and initiating free radical formation. Upon initiation there is a detectable physical or chemical change in the solution, or sol, this being a change in pH, absorbance, phase or surface property, and which is either directly or indirectly related to the concentration of ligand present in the fluid assayed.

DETAILED DESCRIPTION OF THE INVENTION

The present invention describes a free radical based biochemical assay premised on labelling a ligand or ligand-recognition molecule with a free radical forming group. To accomplish this the ligand or ligand-recognition molecule must first be isolated and then covalently attached to the free radical forming group. Alternatively, in some instances it is not necessary to covalently attach a free radical forming group as the ligand or ligand recognition molecule itself is capable of free radical formation.

Ligands are typically, but not necessarily, small molecular weight molecules such as drugs, steroid hormones, and other bioactive molecules. Ligand-recognition molecules are generally but also not necessarily large molecular weight molecules, usually proteins such as antibody. Both can be isolated by following biochemical isolation and purification protocols that are characteristically unique for a specific substance, or, in some instances, they can be purchased commercially.

Antigen and antibody are preferred embodiments of a ligand and ligand-recognition molecule respectively. Antibodies with exquisite antigenic specificity can be produced by immunization of animals with antigen, either alone or with adjuvant. For poor antigenic substances, particularly steroids or small peptides, in addition to injecting adjuvant, it is often necessary to couple these ligands to an antigenic carrier as described by R. C. Jenkins and E. C. Sandburg, in the *Methods of Enzymology*, Vol. 15, p. 351, Ed. Raymond P. Clayton, Academic Press, 1969. Generally the carrier is a large molecular weight protein, such as bovine serum albumin. Coupling of the ligand prior to immunization results in antibody against the ligand as well as the carrier. The latter is not used for the assay.

Regardless of whether a ligand alone is used for immunization or is coupled to an antigenic carrier, antinumber of techniques as described by Yalow and Berson supra, and as described by Wide in "Use of Particulate Immunosorbents in Radioimmunoassay", p. 203 (1981), in *Methods of Enzymology*, Vol. 73, Part B, Eds J. Langone and H. Vinakis, Academic Press. Four satisfactory but not exclusive separation techniques are: precipitation of the ligand/ligand-recognition molecule complex with either 50% saturated ammonium sulfate; or, second, precipitation with an antibody that recognizes the ligand-recognition molecule, to which the ligand is bound. The third technique removes labelled or non-labelled ligand that is not bound to the ligand-recognition molecule by absorption of the ligand to one of several possible absorbants, particularly charcoal, talc, or zirconyl phosphate. Lastly, when either the ligand or ligand-recognition molecule is fixed to a solid surface, the site of complex formation, unbound reactants can be removed simply by washing.

After the labelled ligand/ligand-recognition molecule complex is separated from unbound reactants, the amount of label present in the ligand/ligand-recognition molecule complex is determined by resuspending the complex in an organic or aqueous solvent containing reagents which undergo a chemical reaction upon free radical initiation that is detectable, directly or indirectly, as a physical or chemical change of the solution, particularly, but no exclusively, a change in pH, absorbance, phase or surface tension.

Where pH is the parameter being measured the free radical forming complex is resuspended in an organic solution containing a halogenating agent. Cyclohexane is a particularly useful solvent, but any organic solvent capable of being halogenated is suitable as described by Karasch and Brown in the *Journal of Organic Chemistry*, Vol. 61, p. 2142 (1939). Halogenation is accomplished by chlorinating agents such as sulfuryl chloride. Initiation of free radical formation associated with either the ligand or ligand-recognition molecule is accomplished as described by Kharasch and Brown, supra, or by other methods well known to those familiar with the art, that is by physical stimuli, particularly radiation, heat, or chemical initiators, (i.e. peroxides metal compounds such as silver salts), or a combination of physical and chemical treatments. Generally a combination of physical and chemical initiation is preferred as shorter reaction times and higher yield of free radical result. Upon initiation of free radical formation associated with the ligand or ligand-recognition molecule a reaction is induced between the organic solvent and halogenating agent to cause a decrease in the pH of the solution.

In those instances where the solution properties being measured are changes in absorbance, or phase or surface tension the ligand/ligand-recognition molecule complex can be contacted with an aqueous sol containing a monomer of a polymerizable organic molecule and a surface active agent. Typically usable monomers are sytrene, ethylene or propylene. A variety of long or short chain detergents are suitable surface active agents particularly potassium or sodium laurate or myristate. The detergents are used at their critical micelle concentration which is ascertainable from the work of Harkins in "A General Theory of the Mechanism of Emulsion Polymerization", *Journal of Organic Chemistry*, Vol. 69, p. 1428 (1946). Free radical initiation is induced with typical water-soluble peroxides, particularly sodium or potassium persulfate. The latter causes the formation of a free radical associated with the ligand/ligand-recognition molecule complex that reacts with the hydrocarbon monomers to cause polymerization. The latter "removes" detergent molecules from solution which is measurable as a change in surface tension using the capillary rise method as described by Levine in *Physical Chemistry*, pgs. 325–326, Eds. D. C. Jackson and Mc Gardman, McGraw-Hill Inc. (1978), or as a change in the absorbance or phase properties of the solution. The latter is assayed with the aid of a spectrophotometer, or fluorescent dyes whose solubility is dependent on detergent concentration as described by Harkins, supra. Additionally, absorbent or phase changes can be assessed turbidmetrically as described by Levine, supra, or Stearms in *The Journal of Chemical Physiology*. Vol. 15 (1947).

The following examples are given to aid in understanding the invention but the invention is not limited to the particular procedures, conditions or materials of the examples.

EXAMPLE 1

Assay for ligands in fluids using ligands labelled with free radical forming groups, and detection based on free radical induced pH changes—indirect assay

LIGAND/LIGAND-RECOGNITION MOLECULE COMPLEX FORMATION

Rabbit antisera is raised and isolated, as described essentially by Abraham in *Abraham In Acts Endocrinology*, Vol. 75, p. 1, Sup. 183 (1974), against estrone-3-sulfate to produce an antibody which can competitively bind both estrone-3-sulfate, and its free radical forming derivative, estrone-3-sulfonyl-benzoyl peroxide. The former was obtained commercially, while the latter is produced by reacting estrone-3-sulfuryl chloride with benzoyl chloride in an alkaline, aqueous solution of hydrogen peroxide. Next, a constant amount of anti-estrone-3-sulfate rabbit antibody is added to several 12×75 mm test tubes containing 1 ml of pH 7.4 phosphate buffered solution such that the antibody binds 50% of a 1000 pg standard of estrone-3-sulfate. A 1000 pg aliquot of estrone-3 sulfonyl-benzoyl peroxide is added to each tube, followed either by the addition of known amounts of estrone-3-sulfate which varies from 5 to 1000 pg, or an aliquot of fluid containing an unknown quantity of estrone-3-sulfate. The tubes are allowed to incubate for two hours at 10° C. at which time an empirically determined amount of second antibody, goat anti-rabbit, is added to separate the bound ligands from their unbound counterparts. The tubes are spun at low speed in a clinical table top centrifuge, and the supernate discarded.

FREE RADICAL FORMATION AND REACTION

Derivation of a standard curve relating changes in pH to ligand concentration, and its use to determine the concentration of ligand in fluids sought to be assayed.

Since the amount of estrone-3-sulfonyl benzoyl peroxide present in the ligand/ligand-recognition molecule complex is algebraically related to known amounts of estrone-3-sulfate used to compete with estrone-3-sulfonyl-benzoyl peroxide for binding to the antibody, a standard curve can be constructed and used to ascertain the amount of ligand present in the fluid sought to be assayed.

To construct a standard curve and determine the amount of ligand present in a fluid containing unknown amounts of ligand the residuals left in each tube above are dissolved in 1 ml of cyclohexane containing 0.05 to 0.2 moles of sulfuryl chloride. The tubes are heated to 100° C. to cause the following reaction:

where RH is cyclohexane. The HCl generated causes a decrease in pH of the solution which can be measured by pH meters, or by including a pH indicator in the solution. The concentration of HCl generated is dependent upon the number of free radicals released when the solution is heated. Thus, a relationship exists between the original concentration of free radical forming groups in the ligand/ligand-recognition molecule complexes present in the residuals of each tube, and the decrease in pH. A standard curve is then constructed which relates the changes in pH to the known amounts of estrone-3-sulfate used. Finally, the pH of the fluid containing ligand sought to be assayed is noted, and by extrapolation using the standard curve the amount of estrone-3-sulfate present is determined.

EXAMPLE II

Assay for ligands in fluids using ligands labelled with free radical forming groups and detection based on free radical induced pH changes—indirect assay

LIGAND/LIGAND-RECOGNITION MOLECULE COMPLEX FORMATION

Rabbit antisera is raised and isolated as described in Example I against estrone to produce an antibody which can competitively bind both estrone and the free radical forming group estrone-6-polystyrene. The former can be purchased commercially with estrone-6-polystyrene was produced by taking estrone-6-amine and coupling it to a small molecular weight polystyrene molecule by use of a carbodiimide reagent. The remaining procedures were identical to those in Example I.

FREE RADICAL FORMATION AND REACTION

Derivation of a standard curve relating changes in pH to ligand concentration, and its use to determine the concentration of ligand in fluids sought to be assayed.

The residuals left in each tube above are dissolved in 1 ml of an aqueous solution containing 0.005 moles acrylic acid and 0.005 to 0.01 moles of sodium persulfate. The solution is exposed to a UV light source for 15 minutes to initiate free radical formation, and then 0.015 moles of hydroquinone are added to stop the reaction. 1 ml of isooctane is then aliquoted into each tube, and the mixture is allowed to incubate at 10° C. for 2 hours, after which the isooctane is decanted off and the pH measured by means of a pH meter or suitable pH indicator.

Since the amount of acrylic and polyacrylic acid which diffuses into the isooctane layer is dependent on the amount of acrylic acid incorporated onto the polystyrene molecules as a graft polymer, and the number of graft polymers is dependent upon the concentration of the estrone-6-polystyrene, a relationship exists between the amount of acrylic acid that diffuses into the isooctane layer, and subsequent pH.

Similar to Example I, a standard curve is constructed and used to determine the amount of ligand present in the fluid sought to be assayed.

EXAMPLE III

Assay for ligands in fluids using ligand-recognition molecules labelled with free radical forming groups and detection based on free radical induced pH changes—direct assay

LIGAND/LIGAND-RECOGNITION MOLECULE COMPLEX FORMATION

Rabbit antisera is raised and isolated as described earlier against estrone to produce an antibody which can bind estrone. A second antibody, goat anti-rabbit/estrone is raised against complexed anti-estrone and estrone which is incapable of binding to the first antibody unless estrone is bound to it. Estrone is purchased commercially while the ligand-recognition molecule is labelled with a free radical forming group by covalently attaching persulfate anions to the second antibody. This is accomplished by an anhydride reaction utilizing the hydroxyl groups of several of the amino acid residues on the antibody and reacting them with chloropersulfate in pyrydine. A standard concentration of first antibody (anti-estrone) is covalently attached to a paper fiber strip by the method of C. F. Chang and V. L. Estergreen, *Steroids*, Vol. 41, Number 2, p. 173 (1983), and such methods are hereby incorporated by reference. The concentration of the anti-estrone is such that the antibody can bind a 1000 pg standard of estrone when the fiber strip is dipped into a test tube containing estrone in 1 ml of pH 7.4 phosphate buffered solution. Next, to a series of 12×75 test tubes containing 1 ml of 7.4 pH phosphate buffered solution is added either known amounts of estrone ranging from 5-1000 pg, or fluid containing an unknown amount of estrone. The tubes are allowed to incubate for 1 hour at 10° C. The second antibody is added to the tubes in an amount capable of binding all the estrone that had been bound previously to the first antibody, and allowed to incubate for 1 hour at 10° C. at which time the fiber strip was removed.

FREE RADICAL FORMATION AND REACTION

Derivation of a standard curve relating changes in pH to ligand concentration, and its use to determine the concentration of ligand in fluids sought to be assayed.

To construct a standard curve, and determine the amount of ligand present in a fluid containing unknown amounts of ligand it is sufficient to follow the procedures in Example I with the following alterations: first, the fiber strip is dipped into cyclohexane and then heated to start the reaction. Second, the peroxide source, rather than being estrone-3-sulfonyl benzoyl peroxide, is the persulfate labelled goat antibody. After completion of the free radical reaction, a standard curve is constructed relating changes in pH to known amounts of estrone, and used to determine the amount of ligand present in the fluid sought to be assayed.

EXAMPLE IV

Assay for ligands in fluids using ligand-recognition molecules labelled with free radical forming groups and detection based on free radical induced pH changes—direct assay

LIGAND/LIGAND-RECOGNITION MOLECULE COMPLEX FORMATION

Rabbit antisera is raised and isolated as described in Example I, against estrone, and a second antibody, goat anti-rabbit estrone is raised against estrone bound to anti-estrone antibody. The second antibody is incapable of binding to the first antibody unless estrone is bound to it. The second antibody is labelled with a free radical forming groups by covalent attachment of polystyrene molecules. This is accomplished by coupling polystyrene to lysine residues of the antibody by use of a carboidimide reagent. A standard concentration of the first antibody (anti-estrone) is covalently attached to a paper fiber strip as described previously in Example III. Subsequent procedures to ensure ligand/ligand-recognition complex formation were identical to Example I.

FREE RADICAL FORMATION AND REACTION

Derivation of a standard curve relating changes in pH to ligand concentration, and its use to determine the concentration of ligands in fluids sought to be assayed.

These procedures were identical to those in Example II.

EXAMPLE V

Assay for ligands in fluids using ligand-recognition molecules labelled with free radical forming groups and detection based on free radical induced pH changes—direct assay

LIGAND/LIGAND-RECOGNITION MOLECULE COMPLEX FORMATION

A standard amount of estrone is covalently coupled to 12×75 mm test tubes containing 1 ml pH 7.4 phosphate buffered solution. The ligand-recognition molecule, rabbit anti-estrone, is labelled with a free radical forming group by covalently coupling persulfate anions as described in Example III. The antibody, along with varying concentrations of estrone from 5 to 1000 pg, is aliquoted to one set of tubes. To other tubes is added antibody and fluid containing an unknown concentration of ligand. The solutions are incubated for 2 hours at 10° C. at which time the fluids were decanted.

FREE RADICAL FORMATION AND REACTION

Derivation of a standard curve relating changes in pH to ligand concentration and its use to determine the concentration of ligands in fluids.

The materials and methods used in Example I were identical to those used in this section with the following exception. The peroxide source is persulfate anions attached to antibody rather than estrone-3-sulfuryl benzoyl peroxide. As in Example I, a standard curve is constructed relating changes in pH to known amounts of estrone, and used to determine the amount of ligand present in the fluid sought to be assayed.

EXAMPLE VI

Assay for ligands in fluids using ligand-recognition molecules labelled with free radical forming groups and detection based on free radical induced pH changes

LIGAND/LIGAND-RECOGNITION MOLECULE COMPLEX FORMATION

The materials and methods used in Examples IV and V were identical to those used in this section with antibody being labelled with the free radical forming group, polystyrene.

FREE RADICAL FORMATION AND REACTION

Derivation of a standard curve relating changes in pH to ligand concentration, and its use to determine the ligand concentration in fluids.

The materials and methods used in Example II are identical to those used here with the following exception: the free radical forming group, polystyrene, is attached to the antibody rather than estrone-6-polystyrene.

EXAMPLE VII

Assay for ligands in fluids using free radical forming groups and detection of ligands based on solution phase changes

LIGAND/LIGAND-RECOGNITION MOLECULE COMPLEX FORMATION

The materials and methods used to synthesize a labelled ligand, estrone-6-polystyrene, and establish complex formation are identical to those of Example II.

FREE RADICAL FORMATION AND REACTION

Derivation of a standard curve relating solution phase changes to the concentration of ligands, and determination of ligands in fluids.

The ligand/ligand-recognition molecule complex formed in Example II is dissolved in 1 ml of distilled water and agitated by sonication in a water bath for 5 to 20 minutes. Next, 0.005 to 0.01 moles of sodium persulfate, 0.05 to 0.1 moles of styrene and 0.024 moles of potassium laurate is added. The tubes are capped and heated to 100° C. for 15 minutes, and then 0.015 moles of hydroquinone is added to stop the reaction. A standard curve is constructed relating the degree of phase change, specifically, the degree of conversion of styrene into a colloidal suspension as it is incorporated into the polystyrene molecules to the different amounts of ligand used. Phase change can be measured by determining changes in the absorbance of the resulting solution.

EXAMPLE VIII

Assay for ligands in fluids using ligands labelled with free radical forming groups and detection based on free radical induced changes in solution surface tension

LIGAND/LIGAND-RECOGNITION MOLECULE COMPLEX FORMATION

The materials and methods used were identical to Example II.

FREE RADICAL FORMATION AND REACTION

Derivation of a standard curve and its use to determine the ligand concentration in fluids.

The methods and materials are identical to those of Example VII with the exception that a standard curve is constructed by relating changes in surface tension to different amounts of ligand. Surface tension is determined using the capillary-rise method.

EXAMPLE IX

Assay ligands in fluids premised on a ligand/ligand-recognition molecule comples. Wherein the preradical forming group is derived from the covalent attachment of ligand and ligand-recognition molecules

LIGAND/LIGAND-RECOGNITION MOLECULE COMPLEX FORMATION

Rabbit antisera is raised and isolated as described in Example I against estrone-3-sulfonyl benzyl peroxide. The later molecule is generated by reacting the ligand estrone-3-chlorosulfate with ligand-recognition molecule benzyl chloride using an alkaline aqueous solution containing an excess of hydrogen peroxide. The assay is performed by adding to a series of 12×75 mm test tubes estrone-3-chlorosulfate over a range of 5–1000 pg, and benzylchloride at a concentration in excess of estrone-3-chlorosulfate. Benzylchloride is also added to additional tubes containing, unknown amounts of estrone-3-chlorosulfate. Next, strips with bound anti-estrone-3-sulfonyl benzyl peroxide antibody constructed as described in Example VIII. With the capacity to bind 1000 pg estrone-3-sulfonyl benzyl peroxide are incubated in the tubes for 2 hours at 10° C. and then removed

FREE RADICAL FORMATION AND REACTION

Derivation of a standard curve and its use to determine the ligand concentration in fluids.

The materials and methods used in Example VIII are similarly used here to derive a standard curve and to extrapolate from it the concentration for ligand present in the fluids containing unknown ligand concentration.

We claim:

1. A method for biochemically measuring the quantity of ligand in a fluid comprising the steps of:
    combining said ligand with a molecule recognizing said ligand to form a ligand recognition molecule complex, wherein said ligand or said ligand recognition molecule is reactive to becoming a free radical, or has associated with it a free radical forming group capable of forming a free radical, wherein said free radical forming group is selected from the group consisting of peroxide, styrene and polystyrene;
    separating said ligand recognition molecule complex from uncomplexed ligands and ligand recognition molecules;
    contacting said separated complex with a solution containing a component having properties that are changed by reaction with said free radical;
    physically and/or chemically acting on said ligand recognition molecule complex to generate free radicals for action on said component; and
    measuring the change in properties of said solution and determining the quantity of ligand by comparison with the change in properties induced by known quantities of a ligand in a separate procedure.

2. A method according to claim 1 wherein said change in said solution is an optical change.

3. A method according to claim 1 wherein said free radical formation is induced chemically by addition of silver compounds.

4. A method as described in claim 1 wherein said ligands are antigenic.

5. A method as described in claim 4 wherein said antigenic ligands are steroids or proteins.

6. A method as described in claim 5 wherein said antigenic ligands are sex hormones.

7. A method as described in claim 6 wherein said free radical forming group comprises a chemical capable of forming a free radical that is covalently bound to either the ligand or ligand recognition molecule.

8. A method as described in claim 7 wherein said covalent bonding is the product of reacting a free radical forming group with hydroxyl groups of said ligands or said ligand recognition molecules.

9. A method according to claim 4 wherein contacting said separated complex with a solution containing said component comprises a component that exhibits detectable surface active properties upon reaction with free radical molecules.

10. A method according to claim 9 wherein contacting said separated complex with a solution containing a component having properties that are alterable by free radical reaction comprises a halogentable organic solvent containing a halogenating agent that reacts to cause a change in the properties of said solution.

11. A method according to claim 10 wherein free radical formation is induced by heat.

12. A method according to claim 11 wherein free radical formation is induced by light.

13. A method according to claim 12 wherein free radical formation is induced chemically by addition of a free radical.

14. A method according to claim 10 wherein a change in said property of said organic solvent is a decrease in pH.

* * * * *